(12) United States Patent
Gold et al.

(10) Patent No.: US 8,414,846 B2
(45) Date of Patent: *Apr. 9, 2013

(54) DEVICES AND METHODS FOR THE COLLECTION AND DETECTION OF SUBSTANCES

(75) Inventors: Mark S. Gold, Alachua, FL (US); David M. Martin, Lansdale, PA (US); Steven T. Gold, Rydal, PA (US); Bruce A. Goldberger, Newberry, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 683 days.

This patent is subject to a terminal disclaimer.

(21) Appl. No.: 12/208,896

(22) Filed: Sep. 11, 2008

(65) Prior Publication Data

US 2009/0197283 A1    Aug. 6, 2009

Related U.S. Application Data

(60) Provisional application No. 60/971,451, filed on Sep. 11, 2007.

(51) Int. Cl.
*G01N 21/75* (2006.01)
(52) U.S. Cl. .................................................. 422/406
(58) Field of Classification Search .................. None
See application file for complete search history.

(56) References Cited

U.S. PATENT DOCUMENTS

| | | | |
|---|---|---|---|
| 4,260,678 A | 4/1981 | Lepp et al. | |
| 4,343,312 A | 8/1982 | Cals et al. | |
| 4,357,311 A | 11/1982 | Schutt | |
| 4,381,291 A | 4/1983 | Ekins | |
| 4,399,217 A | 8/1983 | Holmquist et al. | |
| 6,197,254 B1 | 3/2001 | Silver et al. | |
| 6,228,658 B1 | 5/2001 | Formica et al. | |
| 6,514,773 B1 | 2/2003 | Klein et al. | |
| 6,524,530 B1 | 2/2003 | Igarashi et al. | |
| 7,507,374 B2 * | 3/2009 | Gould et al. ................. 422/417 |
| 7,955,572 B2 * | 6/2011 | Hannant et al. ................ 422/406 |
| 2005/0084842 A1 * | 4/2005 | O'Connor ........................... 435/4 |
| 2005/0136553 A1 * | 6/2005 | Kaylor et al. .................. 436/518 |
| 2005/0177072 A1 * | 8/2005 | Kloepfer et al. .............. 600/583 |
| 2007/0231923 A1 | 10/2007 | Cumberland et al. | |
| 2008/0260581 A1 * | 10/2008 | Rosman et al. .............. 422/68.1 |
| 2009/0004058 A1 * | 1/2009 | Liang et al. .................. 422/68.1 |
| 2010/0129922 A1 * | 5/2010 | Gold et al. ....................... 436/96 |

FOREIGN PATENT DOCUMENTS

| | | |
|---|---|---|
| EP | 0 942 278 | 9/1999 |
| WO | WO 97/10499 | 3/1997 |
| WO | WO 98/42252 | 10/1998 |

OTHER PUBLICATIONS

Santra et al., "Synthesis and Characterization of Fluorescent, Radio-Opaque, and Paramagnetic Silica Nanoparticles for Multimodal Bioimaging Applications", *Advanced Materials*, Sep. 2005, vol. 17, Issue 18, pp. 2165-2169.

* cited by examiner

*Primary Examiner* — Ann Lam
(74) *Attorney, Agent, or Firm* — Saliwanchik, Lloyd & Eisenschenk

(57) ABSTRACT

The present invention is a single self-contained device for collecting, transferring, extracting, and testing for the presence of a target analyte in a sample obtained from a surface by swabbing, solid materials (pills, capsules, unknown powders), air samples and biological and non-biological fluids. The device includes a swab, a retention well including eluent fluid, and analysis technologies which can include but are not limited to lateral flow testing analysis. The major improvement is the invention of rinsing the swab with proprietary elution fluid prior to testing thereby not compromising the chemistry and allowing for a wide variety of applications under extremely hot or cold field conditions. Also, the device is in one self-contained unit instead of having a separate water dropper or spray. Moreover, the shape of the device is similar to a magic marker so it is more substantial than any drug tester on the market, as well in certain embodiments it can have grips resembling a gun and in certain embodiments can even emit sounds or smells when a surface is wiped or a positive test is attained.

15 Claims, 13 Drawing Sheets
(8 of 13 Drawing Sheet(s) Filed in Color)

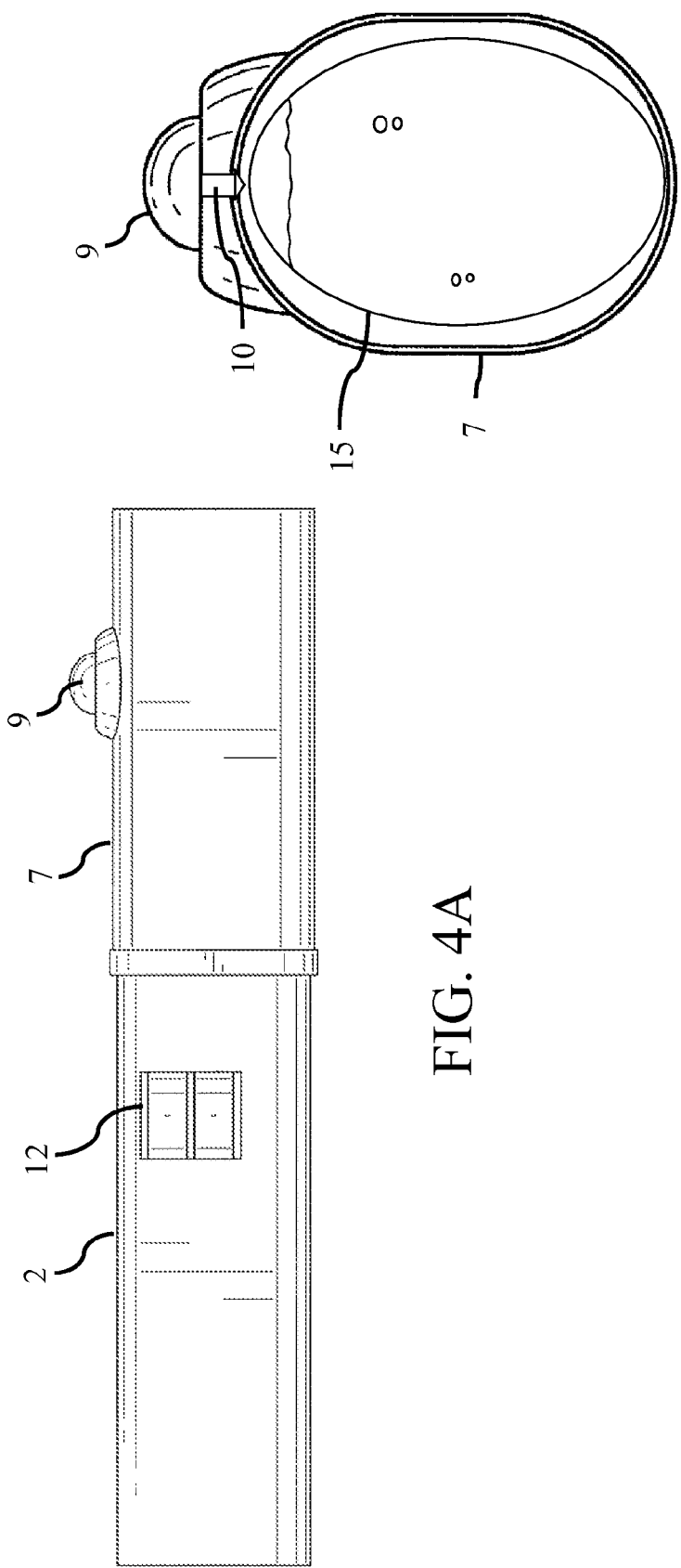

LABEL AREA

COLOR VARIATION

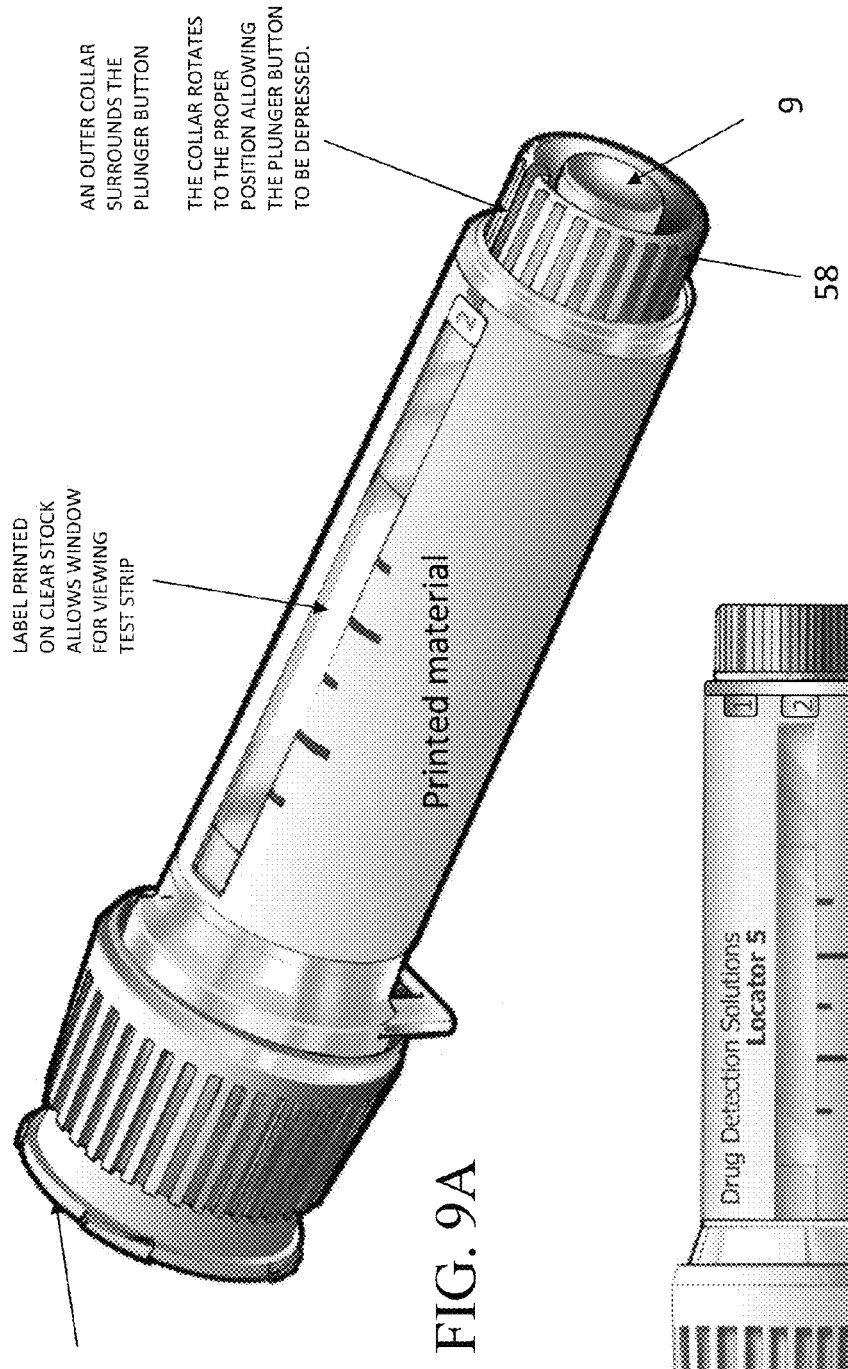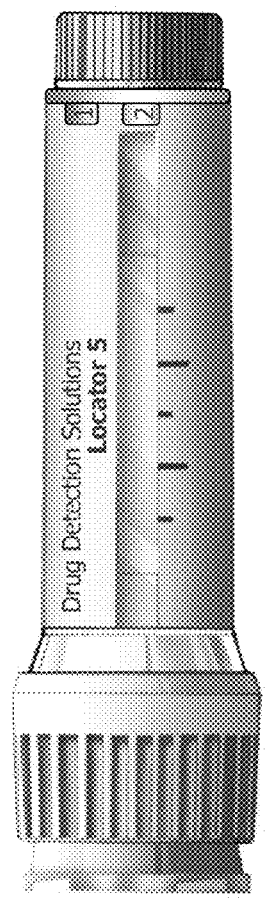
FIG. 9A
FIG. 9B

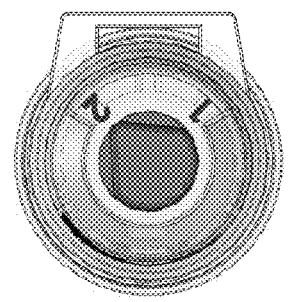
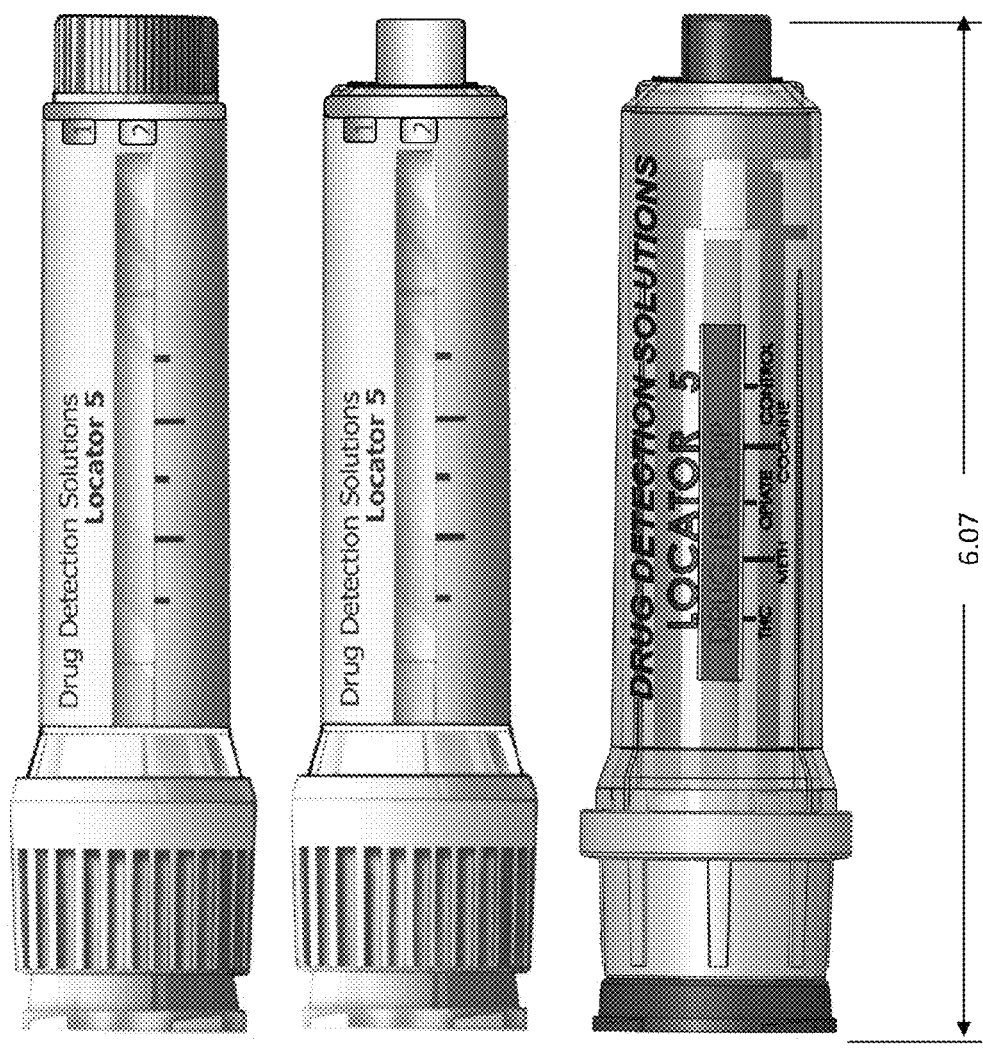
FIG. 10A  FIG. 10B  FIG. 10C  FIG. 10D

DEVICES AND METHODS FOR THE COLLECTION AND DETECTION OF SUBSTANCES

CROSS-REFERENCE TO A RELATED APPLICATION

This application claims the benefit of U.S. provisional patent application Ser. No. 60/971,451, filed Sep. 11, 2007, which is incorporated herein, in its entirety, by reference.

BACKGROUND OF THE INVENTION

The rapid and accurate detection of visible and invisible substances, including target molecules and microorganisms is critical for many areas of research, environmental assessment, food safety, medical diagnosis, air quality assessment, homeland security, illicit drug identification, and warfare. In fact, diagnostic assays of biological compounds have become routine for a variety of applications, including medical diagnosis, forensic toxicology, pre-employment and insurance screening, and foodborne pathogen testing.

Industrial demand for low-cost, sensitive, rapid assays with the potential for screening multiple analytes simultaneously or in rapid succession has caused the development of many testing systems and formats. Most systems can be characterized as having three key components: a probe that recognizes the target analyte(s) with a high degree of specificity; a reporter that provides a signal that is qualitatively or quantitatively related to the presence of the target analyte; and a detection system capable of relaying information from the reporter to a mode of interpretation.

To ensure accuracy, the probe (e.g., antibody or nucleic acid sequence) should interact uniquely and with high affinity to the target analyte, but be non-reactive to non-targets. In order to minimize false positive responses, the probe should be non-reactive with and have no cross-reaction to non-target analytes.

Often, a label is directly or indirectly coupled (conjugated) to the probe. The label provides a signal that is related to the concentration of analyte upon completion of the assay. Ideally, the a label is not subject to signal interference from the surrounding matrix, either in the form of signal loss from analyte extinction or by competition from non-specific signals (noise) from other materials in the system.

A detector is usually a device or instrument used to determine the presence of the reporter (and therefore the analyte) in a sample. Some devices utilize a detector that provides an accurate and precise quantitative scale for the measurement of the analyte. Other devices, such as rapid on-site tests, such as pregnancy tests, utilize a detection instrument that provides the test results as a qualitative (positive or negative) signal. This signal may be visual.

Immunochromatographic assays have been known in the art for some time. These include, but are not limited to, lateral flow tests (e.g., lateral flow strips), for detecting analytes of interest. A typical lateral flow test utilizes the concept of lateral liquid or suspension flow in order to transport a given sample to the test. The benefits of lateral flow tests include a user-friendly format, rapid results, long-term stability over a wide range of climates, and relatively low cost to manufacture. These features make lateral flow tests well-suited for applications involving drug testing in urine and saliva in the workplace or retail markets, rapid point-of-care testing in hospitals and doctor's offices, as well as testing in the field for various environmental and agricultural analytes.

Most lateral flow tests are directed to fluid samples and may require several separate materials or parts in a kit in order to perform and/or optimize detection of a target analyte. Current lateral flow tests require some means for collecting the sample and then a means of exposing the sample to probes specific to the target analyte. Urine samples for drug testing are normally collected into a container and then the lateral flow strip is dipped into the sample. The sample travels up the lateral flow strip and if a drug is present binds to available antibodies which causes a reaction that can be visually detected on the strip. Applying this technology to surface, air and fluid testing has been problematic resulting in cumbersome testing procedures that have limitations. For example, applying the sample to be tested directly to the lateral flow strip disturbs the flow of the materials on the strip and hence the results of the test. Applying the sample directly to the lateral strip also limits the areas available to be tested to clean dry areas where there no grease or other debris is present to interfere with the flow on the strip. Also, the material supplied to initiate the reaction, distilled water droplets from a separate water dropper, freezes and as such the test can not be performed in below freezing climates. Moreover, having a separate device for dropping water to initiate the lateral flow reaction is cumbersome, costly and difficult to use for the average officer on the street.

Additional materials that can be provided with the lateral flow test include a separate via containing a buffer solution or water to start the lateral flow reaction, a wick to transport the sample to the test; a filtration material to remove unwanted particles; a conjugate release pad where the detection reagent(s) is immobile when dry but mobilized when wet; and a reaction matrix where the capture reagents are immobilized. Unfortunately, in all of these cases, at least two separate devices (i.e., one device for collecting the sample and another device for detecting target analytes) and multiple steps are required to perform the test. Our invention simplifies and improves upon the previous inventions in this field.

Further, lateral flow tests are frequently subject to flow problems due to the nature of the chemistry and flow of reagents and sample. Any alteration of the test strip can alter the dynamics of the chemistry and reaction of the strip in the present of a target analyte. These tests usually require complex, multipart assays performed on a series of overlapping pads of different types of materials aligned on a test strip. Problems arise from, for example, material incompatibility, contact issues, and imperfect material characteristics. Boundaries found between segments can adversely affect flow characteristics. Different materials may have widely different flow, or wicking, rates, which have different effects on molecules flowing through them. Other problems that exist include contamination of the sample by interfering materials in the matrix, by contact with collector/operator; insufficient sample size due to inadequate "washing"; and operator/collector error when utilizing devices that require multiple devices/parts and steps necessary to test a surface for a target analyte.

Thus, it would be desirable to have a single self-contained device for collecting, extracting, testing, and shipping under forensic chain of custody a sample collected from a surface, air, powder, pill or fluid that is easy to operate and not limited by dirty, greasy or wet contaminates and is stable under a wide variety temperatures and field conditions. The subject invention solves the above limitations in a self-contained device by first collecting samples on a built-in swab and then washing the target analytes off the swab into a temperature stable buffer solution prior to testing. This approach does not limit the type of sample tested as the target analyte does not overload or disrupt the lateral flow technology and is applicable to a wide variety of analytes and detection technologies. While the subject invention has been optimized for the drugs of abuse market, they are not limited to just testing for drugs of abuse and can be used to test for a wide variety of dusts, powders, air, liquids with the same basic device.

BRIEF SUMMARY OF THE INVENTION

The present invention provides a single self-contained device for collecting, extracting, testing, and transferring, under forensic chain of custody, a sample from a medium (e.g., surfaces (hard or soft), air, or fluids) in order to determine the presence or absence of target analytes present on or in the medium. In specific embodiments, the single self contained device of the invention is used to test for the presence of illicit drugs; biohazards; drug-resistant bacteria such as, but not limited to, MRSA, (Methicillin-Resistant *Staphylococcus aureus*); weapons or explosives in a variety of samples.

In preferred embodiments, the subject invention enables an operator to detect, on the spot, target analytes present on or in a medium in a simple manner and without additional technical support (e.g., laboratory equipment or manpower). Preferably, the device of the subject invention provides an observable signal for use in instant testing or continuous monitoring of an analyte in samples taken from a medium. If the target analyte (e.g., illicit drug) is indicated to be present by the subject device and confirmation is required by a laboratory, the entire device (or the cap) is designed for sealing and shipping under forensic chain of custody. The fluid will then be tested by the laboratory to confirm or deny the existence of the substance within the fluid and, thus, from the sample.

In one embodiment, the devices and methods of the subject invention can be used for detecting illegal drugs that are being smuggled or trafficked into or out of a country. This embodiment would be useful for Customs and Border Patrol to monitor activity at land crossings, airports, shipyards, and any other time people or items are crossing a border and require clearance. Analytes can be detected on passports, luggage, airplanes, ships, and in containers. Specifically, the subject device can detect in surface, fluid, or air samples visible, invisible, microscopic, and minute amounts of marijuana, cannabis sativa, cocaine, heroin, amphetamines, MDMA (a.k.a., Ecstasy) and other scheduled and non-scheduled Drug Enforcement Agency drugs of abuse, including prescription drugs of abuse.

In certain embodiments of the invention, a single self-contained device is used to locate the presence of illicit drugs present on solid surfaces such as office furniture, computer keyboards, lockers, trunks of cars, steering wheels, shipping containers, forklifts, work clothing, door knobs, hazmat supplies/protective gear, shipping containers, freight trains, trucking equipment, passports, and baggage. Solid surface detection of drugs of abuse can occur in a wide variety of settings, including, but not limited to employment settings, border crossings, airports, schools, colleges, courts, athletic contests, home inspections for the sale of a home, home inspections for prospective adoptions, and many other forums.

Alternatively, the subject single self-contained device system can be used to detect target analytes, such as parent drugs and/or metabolites present in air or fluid samples (such as blood, saliva and urine). The device can be designed to test for one specific drug of abuse or one specific explosive or bacteria; multiple drugs or multiple explosives or bacteria; or even a combination of drugs and explosives or drugs and bacteria.

Air and fluid detection can occur in all the same settings as solid surface detection. The single self-contained device can be applied to a wide range of analytes where complex testing is now used that involves several components to complete the test. In one embodiment, the single self contained device comprises a housing unit, wherein the housing unit has a main body. The main body is hollow and comprises (a) collection materials or a swab for collecting a target analyte (e.g., from a solid surface and/or air or removed to test fluid samples); (b) an analysis material (such as but not limited to a lateral flow testing system) that performs the function of providing a surface upon which labeled probes are affixed to provide a detectable response when a target analyte is detected; (c) a solution contained inside of the device which is foil sealed and is punctured by "firing" the cap, i.e. pressing it down, and then the water releases into (d) an eluent fluid retention well, preferably in the cap; and e) a results area that enables the operator to ascertain whether a target analyte has been detected on the analysis material.

A key advantage of the device of the subject invention over previous designs is that in certain embodiments it collects the material from a surface on a specially treated swab and then washes the material off the swab with a custom solution. This wash solution containing the material collected from the surface can be tested using a wide variety of detection technologies including, for example, lateral flow and similar systems. This process allows the device to be used on wet, greasy or dirty surfaces as the material is not directly deposited on the lateral flow strip. This allows for a wider application of the device into a number of environments and facilitates testing of visible, as well as invisible, material.

In addition to assaying for drugs of abuse, explosives, bacteria or other materials on surfaces, air and fluids this invention can be used to identify the medications in pills and capsules or to test unknown powders. In one embodiment, the unknown pill, capsule or powder can be placed into the cap of the device and a solution released into the cap by pushing a plunger. The pill will dissolve as the device is shaken or agitated and medication will be released into the solution. The plunger mechanism can be rotated and the test strip lowered into the solution thereby sampling the medication in the pill that is now dissolved in the solution. In another embodiment, a pill crushing device is placed into the cap to accelerate the dissolution of the pill or capsule.

In the preferred method of use, see FIGS. 6A-D, an operator utilizes the single self-contained invention to detect a target analyte (such as an illicit drug) on or in a matrix(surface, air or fluid) by (a) removing the cap (b) rubbing the swab across the surface or item to be tested or alternatively leaving it exposed to collect target analytes in air (c) replacing the cap (d) rotating a dial on the top of the device to position "1" and "firing" the device, thus pressing it to puncture a foil (or other membrane) sealed compartment inside the device, thereby allowing the swab fluid to be released into the cap (e) shake or agitate the invention to rinse the material on the swab into the fluid (f) rotating the dial on the top of the device to "2" and press to introduce the lateral flow strip or other detection technology into the fluid in the cap. (g) reading the results of the test by visually discerning the presence of a line, indicator or a digital display within the main body of the housing unit.

In certain embodiments, the device emits a sound, like, for example, a gunshot or other sound, when the swab is in use or, alternatively, a ringing or other sound when the presence of the substance testing for is detected. In one example, an unknown powder is tested for cocaine. When the officer wipes the substance a gunshot or another sound goes off and when the test confirms the substance is cocaine an alarm sound rings. In other embodiments, the device emits a smell analogous to the substance testing for. In one example, marijuana is detected and the smell of burning marijuana is emitted by the device. In other embodiments, the device emits a smell unlike the substance testing for. In one example, MRSA is detected and the smell of cinnamon is emitted by the device.

In certain embodiments, see FIG. 1, the single self-contained device includes a removable cap. This cap can be located at one end of the device and collects the eluent, such as, for example, water, which is mixed with the collection substance. This cap can be removed, sealed with a lid, wrapped with evidence tape and shipped back to a laboratory to confirm results. In one embodiment, the single self-contained device comprises a housing unit, wherein the housing unit has a main body and a cap that is adapted to be removably coupled to the main body. The main body is hollow and comprises a) a swab or collection material for collecting a target analyte (i.e., from a solid surface and/or air or fluid samples); an analysis material (such as a lateral flow testing system) that performs the function of providing a surface upon which labeled probes are affixed to provide a detectable response when a target analyte is detected and b) a results area that enables the operator to view whether a target analyte has been detected on the analysis material.

In one embodiment, see FIG. 1, the main body includes an eluent fluid retention well having a single puncturable self-sealing membrane through which a swab can pierce. The method of use is similar to that described above for testing a sample solid surface. Specifically, in a method of use, (a) the swab pierces the puncturable self-sealing membrane of the retention well within the main body to wet the swab; (b) the swab is then removed, causing the membrane to self-seal and prevent any release of eluent fluid from the cap; (c) the wetted swab is brought in contact with a solid surface to be tested, such as by swabbing on the surface to collect a sample or it can be lest exposed to collect target analytes in the air; (d) the swab is then replaced into the main body where it repunctures the self-sealing membrane and is immersed in the eluent fluid; (e) inverting the device several times to wash the sample from the swab into the eluent fluid; (f) through capillary action, moving the sample fluid to a lateral flow based test housed in the main body; and (g) reading the result of the test visually or on a digital display when a target analyte in the sample is detected using the lateral flow based analysis test situated within the main body of the housing unit.

In other embodiments, the cap includes an eluent fluid retention well having a) at least one opening; b) at least one moveable sealing mechanism over the opening that prevents the eluent fluid in the retention well from escaping and coming into contact with the collection/analysis material when the cap is placed over the main body of the housing unit; and c) a release mechanism coupled to the sealing mechanism(s) that, when acted upon by the operator, causes the sealing mechanism(s) to move from the opening and allow the eluent fluid in the retention well to flow through the opening(s) and come into contact with the collection/analysis material.

Alternatively, the cap includes an eluent fluid retention well and a moveable release mechanism. The moveable release mechanism or removable vapor proof foil is preferably the method of releasing the eluent fluid so it can flow freely from the retention well for purposes as described herein.

In a method of use for the embodiments described above, an operator utilizes the self-contained single device system of the invention to detect a target analyte (such as an illicit drug) on a solid surface by (a) releasing the eluent fluid from the retention well by activating the release mechanism(s) on the cap to wet the swab; (b) deactivating the release mechanism to seal remaining eluent fluid in the retention well; (c) removing the cap from the main body of the housing unit; (d) bringing the wetted swab in contact with a solid surface to be tested and swabbing the area to collect a sample or leaving it exposed to collect target analytes in the air; (e) placing the cap over the collection/analysis material and the main body of the housing unit; (f) releasing the eluent fluid from the retention well by activating the release mechanism(s) on the cap; (g) inverting, shaking, or otherwise agitating the device several times to wash the sample into the eluent fluid; (h) deactivating the release mechanism to seal remaining eluent fluid within the retention well; and (i) reading the result of the test visually or on a digital display when a target analyte in the sample is detected using a lateral flow based analysis technology situated within the main body of the housing unit.

In certain embodiments, the swab is treated with a water soluble adhesive that will capture residue from the surface and immediately dissolve in the eluent fluid, thus eliminating steps (a) and (b) above. Alternatively, there may be more than one retention well with appropriate amounts of eluent fluid dedicated for use with step (a) and/or (f) so that it is not necessary to deactivate the releasing mechanism and ensure remaining eluent fluid is delivered back into the retention well. As understood by the skilled artisan, the release mechanism can be automated, where upon activation by the operator, the release mechanism is automatically deactivated after a specific time period to ensure appropriate amounts of eluent fluid are released from and/or returned to the retention well.

The subject invention further provides a method for manufacturing a single self-contained device for collecting, transferring, extracting, and testing for the presence of a target analyte from a sample taken from a solid surface and/or air or fluid samples. In one embodiment, the method comprises providing a housing unit comprising a main body and cap that can be removably coupled to the main body; disposing a collection/analysis material in the housing; disposing a retention well within the cap; and disposing an eluent fluid within the retention well within the cap, wherein the cap includes a means for allowing the eluent fluid to be released from the retention well upon action by the operator.

In particular embodiments, the collection and analysis materials are one and the same, where the single collection/analysis material includes in series, a number of zones (predefined areas): a collection (receiving) zone; a conjugate zone; a reaction zone (also referred to as a detection zone); and optionally, a control zone. A medium is contacted with the collection/receiving zone (e.g., by wiping the collection zone on a solid surface), the collection/receiving zone is contacted with the eluent fluid via operator manipulation of the releasing mechanism on the cap, where the target analyte is washed from the collection/receiving zone into the eluent fluid.

The eluent fluid carries the target analyte through the conjugate zone, which contains free (non-immobilized) probes (e.g., monoclonal antibodies or DNA aptamers) specific for different target molecules. Preferably, the probes are labeled with nanoparticles doped or otherwise associated with differently colored dyes (e.g., red and blue dyed nanoparticles) or conductive particles to effect an electrical signal if positive results are detected. All of these components (potentially including probe-target molecule complexes and excess, and unbound probes) flow onto the reaction zone, which contains immobilized binding agents (e.g., polyclonal antibodies) specific for the target molecules. Preferably, the binding agents immobilized in the reaction zone are present in known amounts, such as in a 1:1 ratio, to facilitate quantification of the reaction, as will be described below.

In certain embodiments of the invention the conjugate and detection zone are one and the same, where probes specific for a target analyte are labeled and bound to collection and/or analysis material. Thus, in certain embodiments, the swab incorporates the analysis material. In other embodiments, a separate analysis material comprising both the conjugate and detection zones are provided separately from the swab.

In certain embodiments, a control zone is provided that contains immobilized binding agents specific for unbound probes, and will serve as a positive control to show that the probes were present in the solution.

The single device system of the invention can collect, transfer, extract, and test for the presence of a target analyte on a solid surface, and/or air or fluid samples, and additionally, be sealed to allow the sample and test to be sent to a laboratory for further testing under forensic chain of custody.

Addition embodiments and advantages of the invention will become apparent from the following detailed description.

The detector in this invention relates a positive or negative test result which is read by the human eye or an optical reading that is computerized which reads the test.

It should be noted that the device can be adapted to hold a wide variety of detection devices and is not limited to lateral flow strips.

BRIEF DESCRIPTION OF THE DRAWINGS

The file of this patent contains at least one drawing executed in color. Copies of this patent with color drawings(s) will be provided by the Patent and Trademark Office upon request and payment of the necessary fee. In order that a more precise understanding of the above recited invention be obtained, a more particular description of the invention briefly described above will be rendered by reference to specific embodiments thereof that are illustrated in the appended drawings. Understanding that these drawings depict only typical embodiments of the invention and are not therefore to be considered as limiting in scope, the invention will be described and explained with additional specificity and detail through the use of the accompanying drawings in which:

FIGS. 4A-B are illustrations of one embodiment of a single self-contained device of the invention, where a removable cap includes a retention well with another form of release mechanism.

FIGS. 9A and 9B show a further specific design embodiment wherein the button is surrounded by a collar that can be rotated to the proper alignment before allowing the button to be depressed or "fired."

FIGS. 10A-D are side views and a top view (FIG. 10D) of several design embodiments of the subject invention, using different button and cap configurations.

FIG. 12A shows a lid configured to fit into the end of the cap. FIG. 12B shows a lid configured to fit on the outside of the cap. FIG. 12C illustrates how the lid, when disengaged from the cap can be used to cover and seal the cap for storage and/or transport.

DETAILED DESCRIPTION OF THE INVENTION

Figure 1:
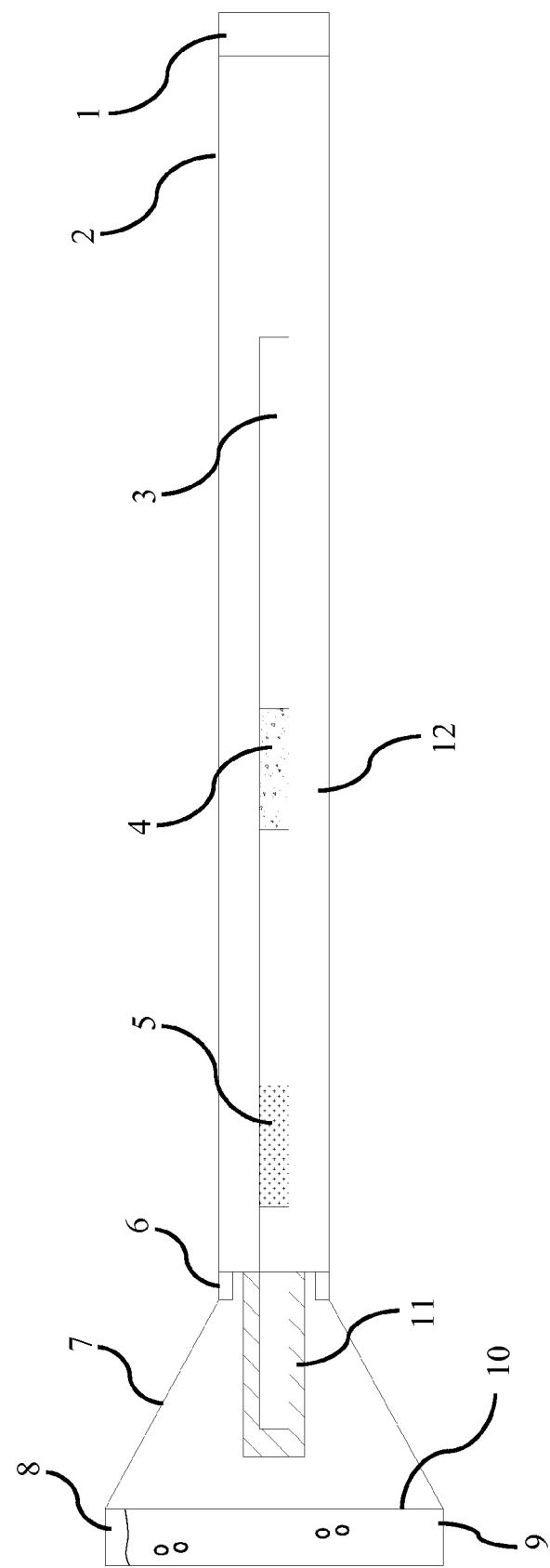
FIG. 1 is an illustration of one embodiment of a single self-contained device of the invention, where a removable cap is coupled to the main body of the housing unit.

The present invention provides a single self-contained device, and materials and methods for manufacturing and using the single device, for collecting, transferring, extracting, and testing for the presence of target analytes from a sample taken from a solid surface and/or from air or fluid samples. Preferably, the single self-contained device is used to detect illicit drug residues (such as residues from marijuana, cannabis sativa, cocaine, heroin, and the like) from solid surface, air, or fluid samples and incorporating the ability to send the device or part of the device for further analysis under forensic chain of custody.

The invention is described herein by reference to several embodiments selected for illustration in the drawings. It should be understood that the spirit and scope of this invention is not limited to the embodiments shown in the drawings or the specific embodiments in the following description. Also, it should be understood that the drawings are not necessarily to scale and that any reference to dimensions or indication of colors in the drawings or the following description are provided for illustrative purposes only and are not intended to limit the scope of the invention in any way.

As used herein, the term "analyte" generally refers to a substance to be detected. For instance, analytes may include, but are not limited to, biological materials, explosives, and illicit and therapeutic drugs. More specifically, analytes include, but are not limited to, toxins, explosive materials, organic compounds, proteins, peptides, microorganisms, amino acids, nucleic acids, hormones, steroids, vitamins, both illicit and therapeutic drugs, drug intermediaries or byproducts, bacteria, virus particles and metabolites of or antibodies to any of the above-substances.

In certain embodiments, the target analytes that the subject device detects include, but are not limited to, explosives such as HMX, RDX, NG, TATB, Tetryl, PETN, TNT, DNT, TNB, DNB, and NC; and biological materials such as antibodies to rubella (including rubella-IgG and rubella IgM), antibodies to toxoplasmosis (including toxoplasmosis IgG (Toxo-IgG) and toxoplasmosis IgM (Toxo-IgM), hepatitis B virus surface antigen (HBsAg), antibodies to hepatitis B core antigen (including anti-hepatitis B core antigen IgG and IgM (Anti-HBC)), human immune deficiency virus 1 and 2 (HIV 1 and 2), human T-cell leukemia virus 1 and 2 (HTLV), hepatitis B e antigen (HBeAg), antibodies to hepatitis B e antigen (Anti-HBe), and influenza virus and bacteria such as drug resistant bacteria, including MRSA.

Preferred embodiments of the invention are directed to the detection of illicit drugs on solid surfaces, pills, capsules, unknown powders, fluids, and in the air. Illicit drugs (including drugs of abuse or controlled substances) that can be detected using the subject invention include, but are not limited to: amphetamine, methamphetamine, MDMA (a.k.a., Ecstasy), barbiturates (such as amobarbital, butalbital, pentobarbital, phenobarbital, and secobarbital), benzodiazepines (such as alprazolam and diazepam); cannabinoids (such as hashish and marijuana), cocaine, fentanyl, LSD, methaqualone, opiates (such as heroin, morphine, codeine, hydromorphone, hydrocodone, methadone, oxycodone, oxymorphone, and opium), phencyclidine, and propoxyphene. In certain embodiments detection of prescription drugs, which are commonly abused, such as pain killers (oxycodone, percocet, etc.) or erectile dysfunction drugs (Viagra™, Cialis™ etc.) may be detected as well as prescription drugs not commonly subject to abuse.

As used herein, the term "sample" generally refers to a material suspected of containing the analyte. The sample preferably contains materials obtained directly from a source or medium. The sample may be derived from a solid or semi-solid surface, pill, capsule, unknown powder, unknown fluids, air, or from a biological source, such as a physiological fluid (including blood, interstitial fluid, saliva, vitreous humor, cerebral spinal fluid, sweat, urine, breast milk, vaginal fluid, menses, and the like).

Preferred samples for testing for illicit drugs are derived from solid surfaces because this form of testing is less intrusive, requires a lower legal standard to test, and because the device is not used directly on humans, FDA clearance is not required. Surface testing for drugs of abuse has been largely ignored in favor of more invasive blood, saliva or urine tests. Surface testing can provide many benefits that biological testing cannot duplicate. In some embodiments, the sample is material derived from wiping residues from a solid surface. Examples of solid surfaces from which a sample may be taken include, but are not limited to, surfaces on office furniture, computer keyboards, lockers, trunks of cars, steering wheels, shipping containers, forklifts, work clothing, door knobs, hazmat supplies/protective gear, shipping containers, freight trains, trucking equipment, fork lifts, passports, and baggage.

The single self-contained device preferably contains a swab and an analysis material based on lateral flow analysis technology. The swab is a solid support of any absorbent material useful in sample collection including, but not limited to, fabric (such as fleece), porous matrices (such as sponge or foam), gel, fiber (such as fiber glass or paper fiber fleeces), cotton, cellulose, rayon, and other synthetic materials. The swab can optionally include materials useful in providing and/or improving solid support of the swab, such as synthetic or semisynthetic polymers (i.e., polyvinyl chloride, polyethylene, polymethyl methacrylate and other acrylics, silicones, polyurethanes, etc.). In certain embodiments, it is preferred that the swab include such supportive materials in order to ensure the swab has the ability to properly penetrate membranes located in certain embodiments of the device. A preferred embodiment is a polyester swab made from 100% unbounded polyester which is treated with Solution (C) containing sodium tetraborate 0.1 molar in a non-ionic surfactant, such as, for example, 1% Triton X-100™ buffer at a pH of 8.6. A preferred embodiment for the eluent inside the tube of the device, which is punctured and released into the cap, is the non-ionic surfactant Triton X-100™ 0.19% with a pH of 7.4. It is a phosphate buffered saline in a preferred embodiment of the water inside the tube inside the body of the device.

The analysis material includes at least one probe that is able to specifically bind to a target analyte such as an illicit drug. The illicit drug must interact with, react to, or bind with the probe (e.g., an aptamer or antibody specific for the illicit drug), which creates some measurable change (temperature, color, current, voltage, etc.). This change is then detected visually or by some transduction mechanism. The degree of change is usually proportional to the illicit drug concentration in the sample taken using the single self-contained device. Analysis material of the invention includes both the detection and transduction mechanisms. For instance, when an illicit drug binds with an antibody specific for the drug labeled with a conductive material (i.e., the probe) and closes an open circuit, the combined materials for the probe and circuit are provided on the analysis material. The closure of an open circuit and flow of current is the transduction mechanism. Colorimetry, reflectance photometry electrical resistance and electrochemistry can be either transduction mechanisms or both binding materials and transduction mechanisms.

In certain embodiments, the probe is labeled so as to communicate to the operator when a target analyte has been bound to the probe. For example, with colorimetric techniques, a labeled enzyme (the label is a compound that is capable of generating a colored product or dye upon binding of the enzyme to a target analyte, such as an illicit drug) is provided on the analysis material. The labeled enzyme is reacted with a target analyte. The amount of colored product generated is directly proportional to the amount of target analyte, such as an illicit drug, present in the sample. Thus, the more illicit drug present in the sample, the more intense the color; whereas the less illicit drug present, the less intense the color.

In certain embodiments, probes of the invention are labeled with chromogenic nanoparticles, which can be produced using known methods (Santra et al., *Advanced Materials*, 2005, 17:2165-2169, which is incorporated herein by reference in its entirety). Highly chromogenic nanoparticles can be generated by a reverse microemulsion method followed by sizing of the particles to select particles with desired diameters (e.g., in the range of 100 nanometers to 400 nanometers). The nanoparticles can be coupled to the binding agents using various chemical groups ($-NH_2$ being the preferred nucleophile). The capture zone can contain immobilized target-specific binding agents in a predetermined amount or ratio (e.g., a 1:1 mixture of two target-specific binding agents). As the concentration of nanoparticles fixed in the capture zone increases, a color indication will be formed that is proportional to the concentration of the captured nanoparticles. If two or more nanoparticles are captured, the resultant color and intensity can be utilized to determine what type of nanoparticles were captured and in what amount.

Reflectance photometry quantifies the intensity of the colored product generated by the enzymatic reaction. A light source, such as a light-emitting diode (LED) emits light of a specific wavelength onto a test strip that includes the colored product (generated as described above). Since the colored product absorbs that wavelength of light, the more a target analyte is present in a sample (and thus the more colored product on the test strip), the less reflected light. A detector captures the reflected light, converts it into an electronic signal, and translates that signal to its corresponding illicit drug concentration.

In certain instances, the probe is coupled to a conductive label to enable electronic signaling to the operator about the presence or absence of a target analyte (such as an illicit drug) in a sample. "Electronic signaling" includes, but is not limited to, a "sensor electrode" or "sensing electrode" or "working electrode," which refers to an electrode that is monitored to determine the amount of electrical signal at a point in time or over a given time period, where the signal is then correlated with the concentration of a target analyte, such as an illicit drug.

The conductive label of the probe can be any of numerous electrically conductive materials such as, but not limited to, platinum-group metals (including, platinum, palladium, rhodium, ruthenium, osmium, and iridium), nickel, copper, silver, and carbon, as well as, oxides, dioxides, combinations or alloys thereof. Some conductive labels and conductive labeled probes and fabrication technologies suitable for the construction of amperometric sensors are known to the skilled artisan and are commonly used in conductive lithography techniques.

According to certain embodiments of the invention, an open circuit is provided with electrodes located at opposite sides of a detection zone on an analysis material. The detection zone consists of immobilized binding agents that have a high specificity and selectivity for the probes of the invention. Preferably, the probes are conjugated to electrically conductive labels. Should a target analyte (i.e., illicit drug) be present in the sample, it will be bound to the conductively labeled probe (i.e., an antibody specific for the illicit drug conjugated to a conductive particle), travel to the detection zone where it will be immobilized by the binding agents, creating a band of conductive-labeled probes/target analyte across the analysis material (such as, for example, a lateral flow test strip). On each side of the lateral flow strip, in the area of the detection zone are two electrodes with a small electrical potential, 0.1-1.0 Volts. The circuit is powered at the beginning of the tests, but no current is able to flow to the electrodes across the detection zone creating an open circuit. Once the test is completed and target analytes, bound to conductively labeled probes, travel to the detection zone, a closed circuit is created. This generates a digital positive signal for the operator to read.

In certain embodiments, a secondary subcircuit is provided. If no target analytes are present in the sample the circuit will not close and after the specific time for the reaction a secondary subcircuit will close indicating a digital negative signal for the operator to read. These signals can be further processed into printed readout, stored in memory or transmitted to a local computer for further signal processing, storage, analysis and reporting. This signal generating process can be done using a variety of lateral flow chemistries, such as, by way of example, competitive binding assays, double antibody and other techniques all generating unique signal patterns for positive and negative findings. The embodiments of the subject invention can be configured to provide space for the above circuitry and other on-board electronics in the main body of the device.

The electrode can be, for example, a Platinum (Pt)-comprising electrode configured to provide a geometric surface area of about 0.1 to 3 $cm^2$, preferably about 0.5 to 2 $cm^2$, and more preferably about 1 $cm^2$. This particular configuration is scaled in proportion to the analysis material and housing unit used in the testing system of the present invention. The electrode composition is formulated using analytical- or electronic-grade reagents and solvents, which can ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants and the solvents in particular are selected for high volatility in order to reduce washing and cure times. Some electrode embodiments are described in European Patent Publication 0 942 278 A2, published Sep. 15, 1999, herein incorporated by reference in its entirety.

Any suitable electrode system can be employed; an exemplary system uses a silver or silver/silver chloride (Ag/AgCl) electrode system. Reference and counter electrodes are formulated typically using two performance criteria: (1) the electrodes are capable of operation for extended periods, preferably periods of up to 24 hours or longer in cases where repeated measurements are necessary, as might be the case in open areas; and (2) the electrodes are formulated to have high electrochemical purity in order to operate within the present system, which requires extremely low background noise levels. The electrodes must also be capable of passing a large amount of charge over the life of the electrodes. With regard to operation for extended periods of time, Ag/AgCl electrodes are capable of repeatedly forming a reversible couple, which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition, which is not susceptible to attack (e.g., plasticization) by components in the eluent fluid sample. The electrode compositions are also typically formulated using analytical- or electronic-grade reagents and solvents, and the polymer binder composition is selected to be free of electrochemically active contaminants, which could diffuse to the sensor to produce a background current. Suitable exemplary sensing electrodes that can be used in accordance with the present invention are described in PCT Publication Nos. WO 97/10499, published 20 Mar. 1997 and WO 98/42252, published 1 Oct. 1998, both of which are incorporated by reference in their entirety.

In one embodiment, the analysis material includes labeled probes that are specific for a target analyte (present in the conjugate zone) and binding agents specific for the bound probes immobilized on the analysis material (present in the reaction zone). When in solution, the labeled probes bind with target analytes and diffuse along the analysis material to react with a line of binding agents immobilized on the analysis material. The binding of the labeled probes with the binding agents provides a line of color or conductively closes an open electrical circuit that provides a visual indication in the results area that communicates to the operator that the target analyte is present. If no target analytes are present in the sample, the colored or conductive probes are not captured by the predisposed immobilized binding agents and no color or closed electrical circuit is on the analysis material, thereby communicating to the operator that the target analyte is not present in the sample.

In another embodiment, the analysis material comprises labeled probes that are immobilized along an area of the analysis material that is visible under the results area. The immobilized labeled/conductive probes are specific for a target analyte and are not visible to the operator when unbound. Upon binding to a target analyte, the labeled probes are visible to the operator or close an electrical circuit via the results area as described above.

The analysis material can be any known test pad containing one or more chemicals, adapted to come into contact with a fluid sample to be tested for an illicit drug. Conventional analysis materials that can be used in combination with the subject invention include, but are not limited to, chemical strip tests used to test for amphetamines, barbiturates, benzodiazepines, cannabinoids, cocaine, opiates and phencyclidine. In specific embodiments of the invention, the parent compound of the illicit drugs such as THC ($\Delta^9$-tetrahydrocannabinol), cocaine and heroin are detected using the device to indicate the presence of the drug in the area tested.

Figure 2:
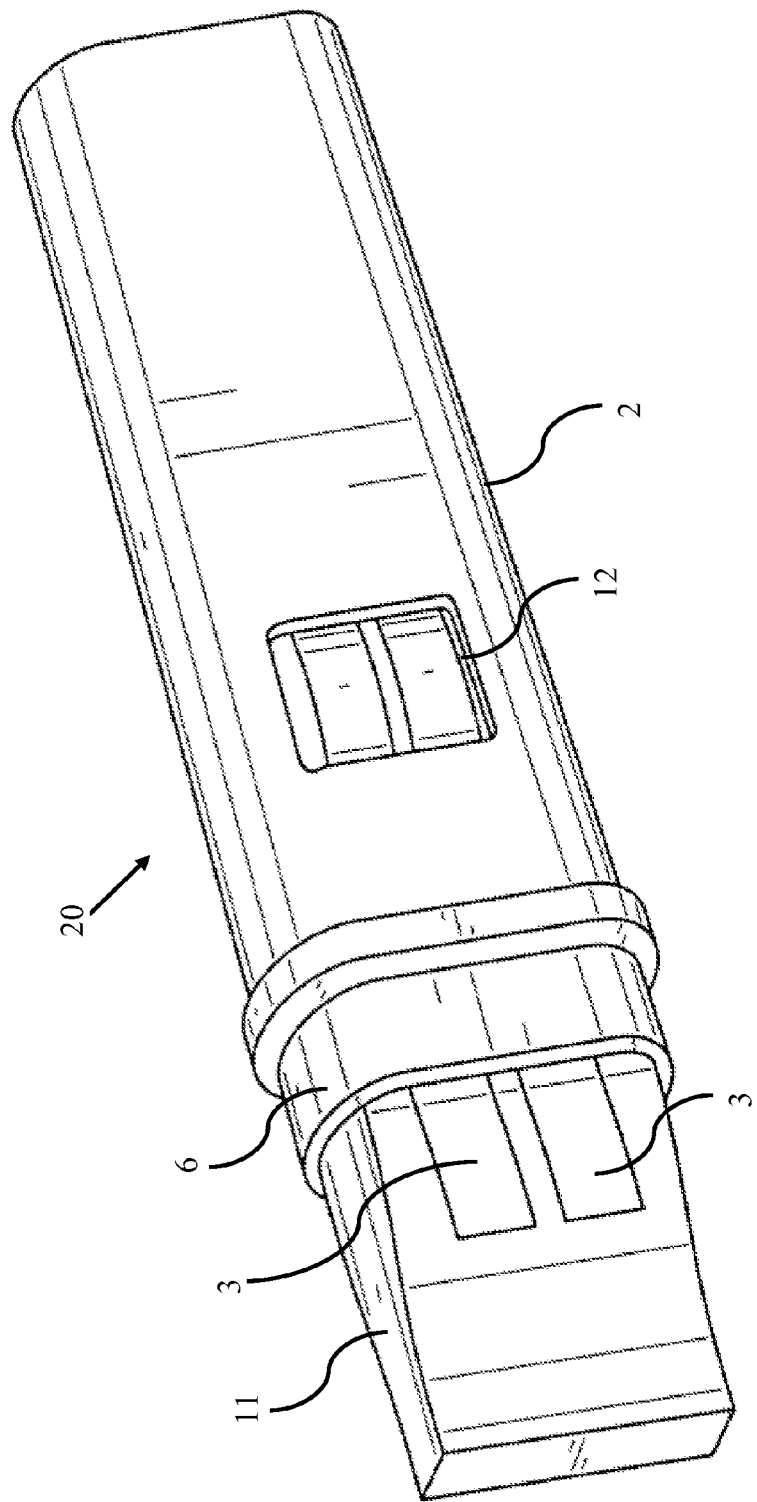
FIG. 2 is an illustration of a single self-contained device of the invention, where the cap has been detached from the main body of the housing unit.
Figure 3C:
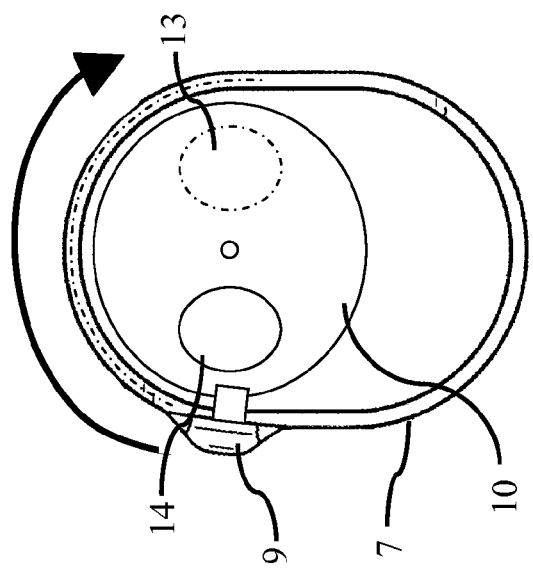
FIGS. 3A-C are illustrations of one embodiment of a single self-contained device of the invention, where a removable cap includes a retention well with one form of release mechanism.
Figure 3A:
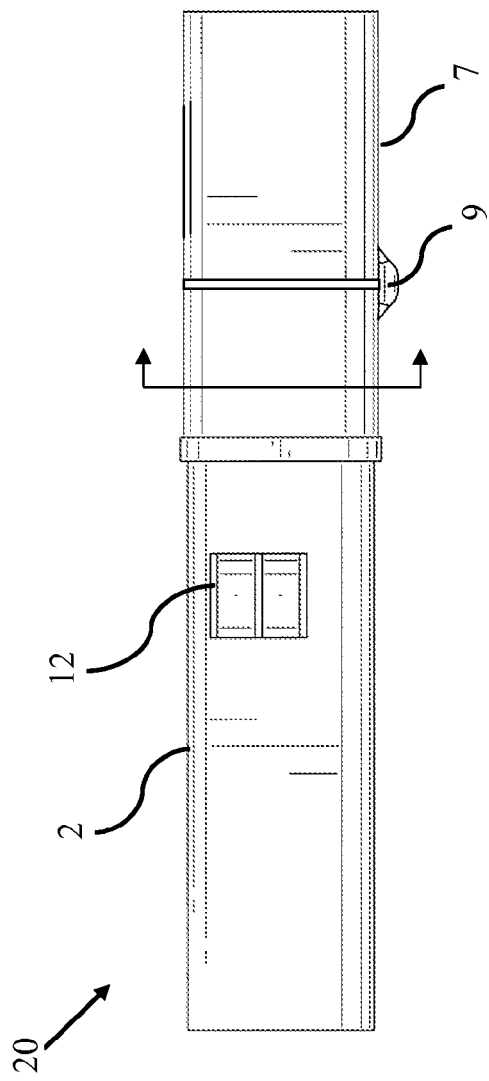
Figure 3B:
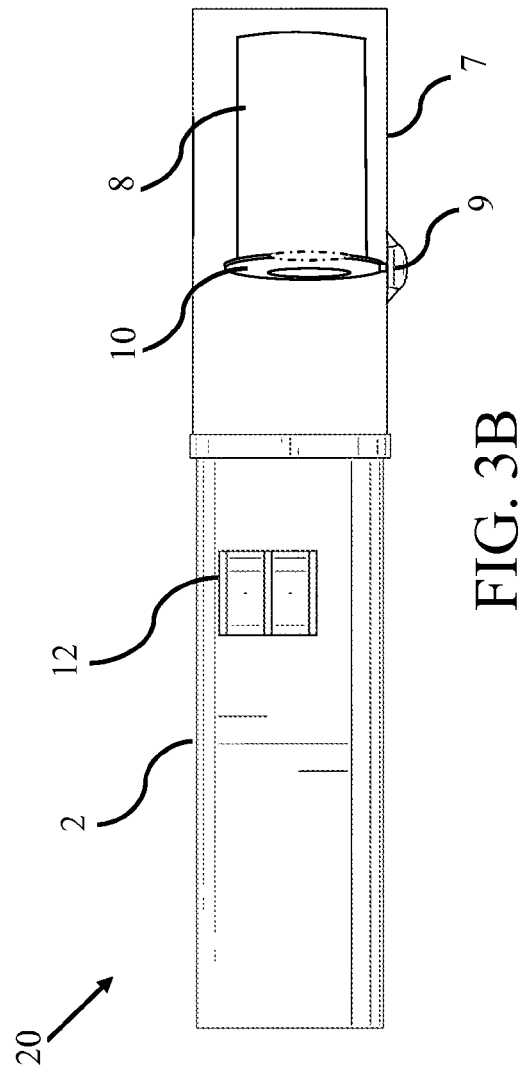

As illustrated in FIGS. 2 and 3A-B, a housing unit 20 is provided, wherein the housing unit has a main body 2. In certain instances, a detachable cap 7 is provided that is adapted to be removably coupled to the main body. In a specific embodiment, the housing unit has the following dimensions: 12 cm×2.5 cm×1 cm. In another specific embodiment, shown, for example, in FIGS. 6A-12, the entire unit is approximately 6.0 inches to approximately 6.5 inches in length.

In a further embodiment, the cap can be removed and sealed with a lid 16, wrapped with evidence tape and shipped back to a laboratory to confirm results. In a particular embodiment, the lid 16 can be form-fitted or capable of nesting with the cap so that it is easily transportable with the device of the subject invention and readily accessible to seal the cap. FIGS. 6A-D, 8, and 12A-C illustrate a specific embodiment having a lid 16 nested within the cap 7 for storage.

In one embodiment, the main body 2 is, in general, a hollow tubular container that can have therein or attached thereto a) a swab 11 used for obtaining a sample (i.e., from a solid surface and/or air or fluid samples); b) an analysis material 3 that performs the function of providing a surface or material upon which labeled probes (and in certain instances, binding agents) are affixed or embedded to provide a detectable response when a target analyte is present; and c) a results area 12 FIGS. 2 and 3 that enables an operator to visually determine whether a target analyte has been detected by the labeled probes or binding agents present on the analysis material.

In one embodiment, the swab 11 in FIG. 2 is removable from the main body 2 when used in testing fluid samples. In a further embodiment, removing the swab 11 exposes at least a portion of the analysis material 3. In a specific embodiment, the analysis material functions on the basis of lateral flow technology or capillary action. In one embodiment, the analysis material can be brought into contact with a fluid to be tested, such as, for example, by dipping the appropriate end of the housing into the fluid sample. In a further embodiment, the detachable cap 7 shown in FIG. 5B, comprises is sufficiently hollow or is designed with a depression or retention well 8 therein, such that a fluid sample can be placed into the cap 7. The main body 20 can be affixed to the cap, which would cause the fluid sample to be placed into contact with the analysis material 3, particularly by inverting the complete housing unit 20. The results of the test can then be observed in the results area on the main body 2. In one embodiment, the test results are provided by use of a direct visual indicator, such as, for example, target analyte activated color or shape indicators. In an alternative embodiment, test results can be displayed on a digital display apparatus triggered when a target analyte in the sample is detected using the analysis material 3.

Figure 5A:
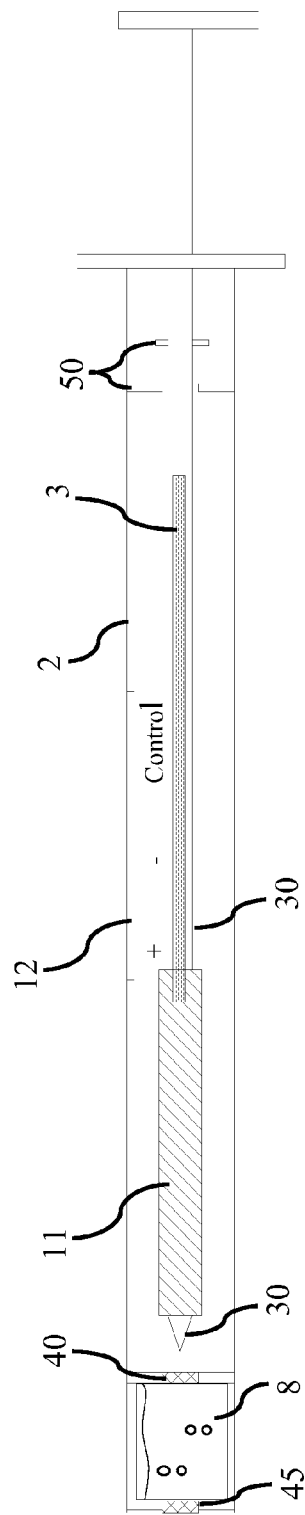
FIGS. 5A-B are illustrations of alternative embodiments of a single self-contained device of the invention.
Figure 5B:
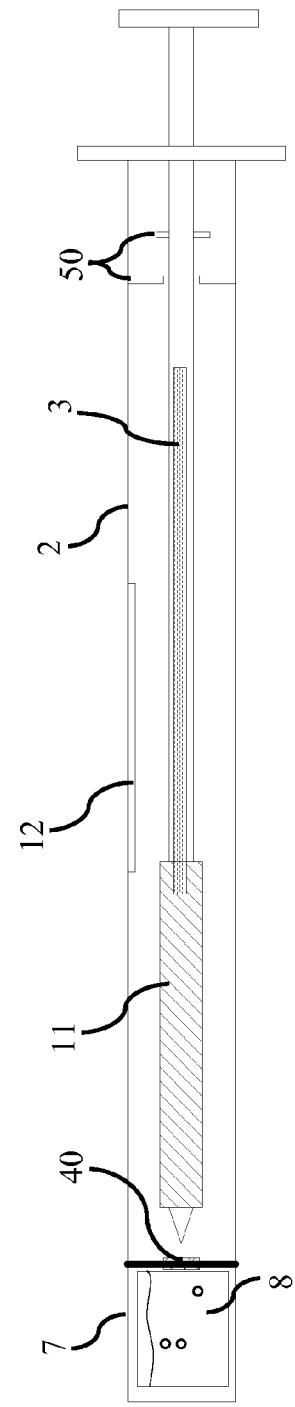
Figure 6A:
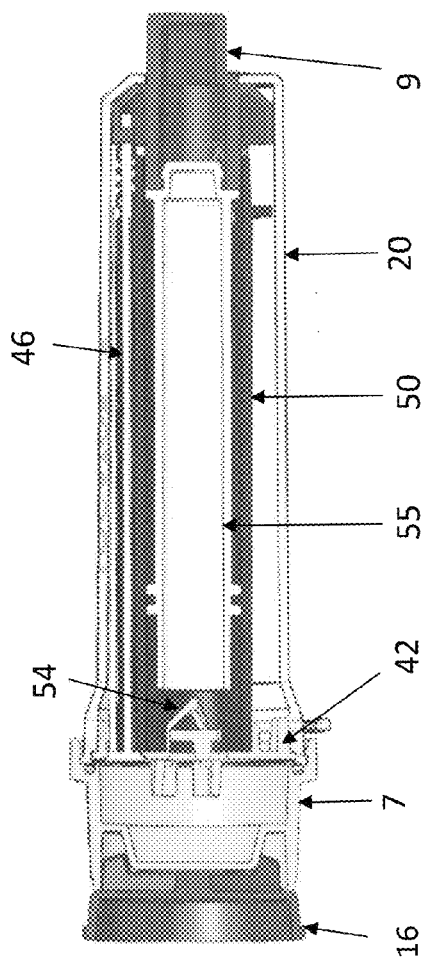
FIGS. 6A-D are cross-sectional illustrations of a specific design embodiment of a single self-contained device of the subject invention. Shown in these figures are the use of a nested lid, an inner tube with fluid retention tube therein, being puncturable with a prong when advanced by the button.
Figure 6B:
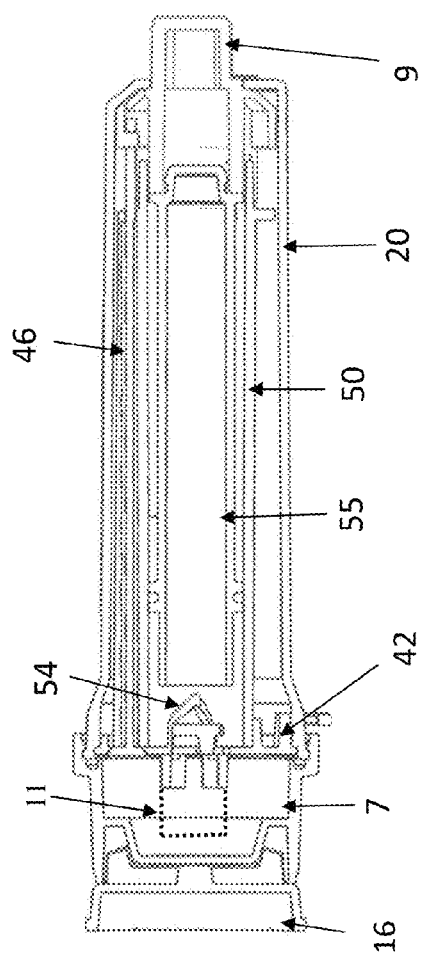
Figure 6C:
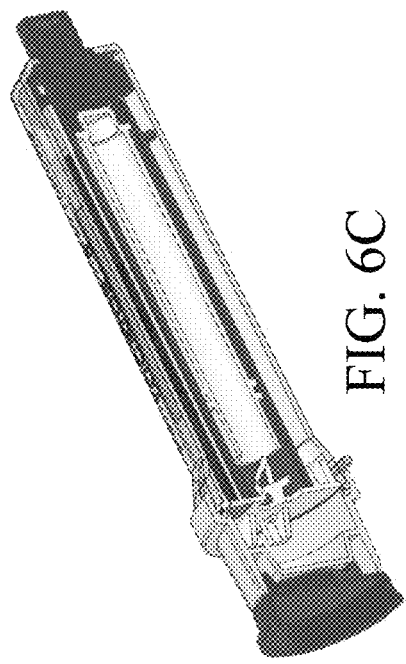
Figure 6D:
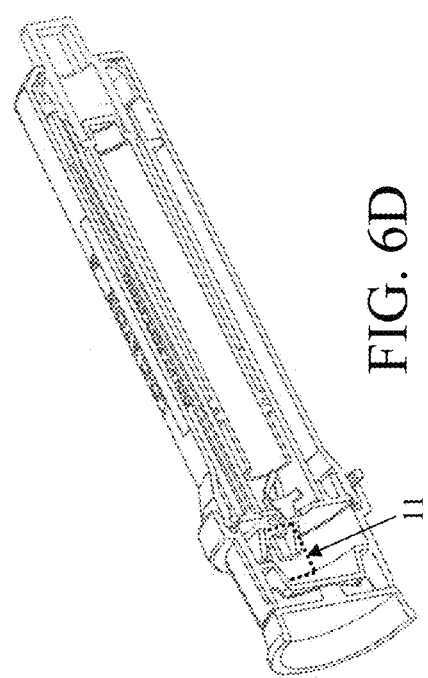
Figure 7C:
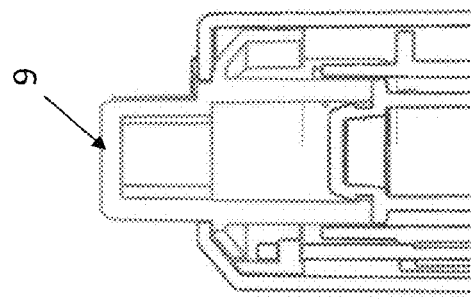
FIGS. 7A-C illustrate an alternative embodiment of a button, with FIG. 7C being a cross-sectional diagram.
Figure 7A:
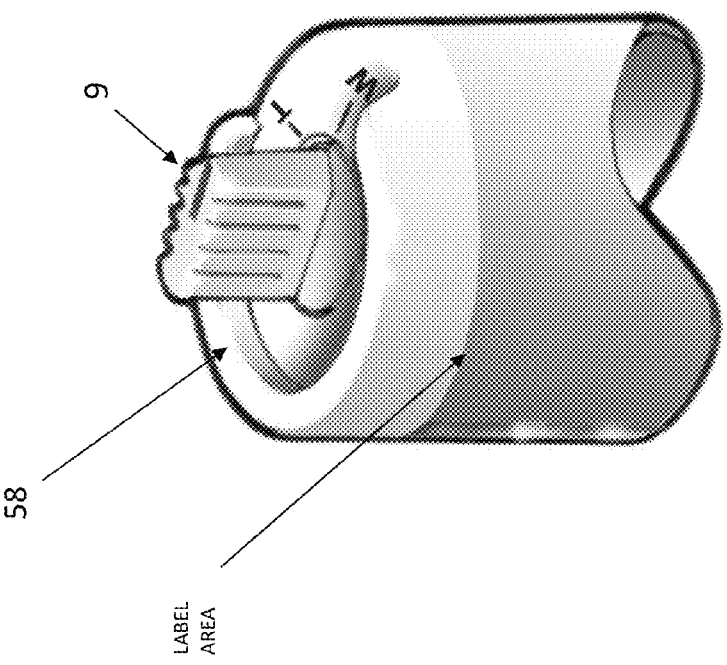
Figure 7B:
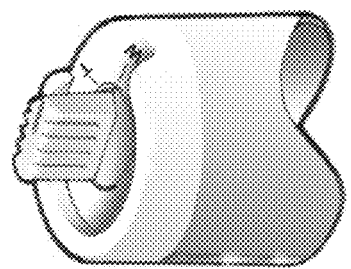
Figure 8:
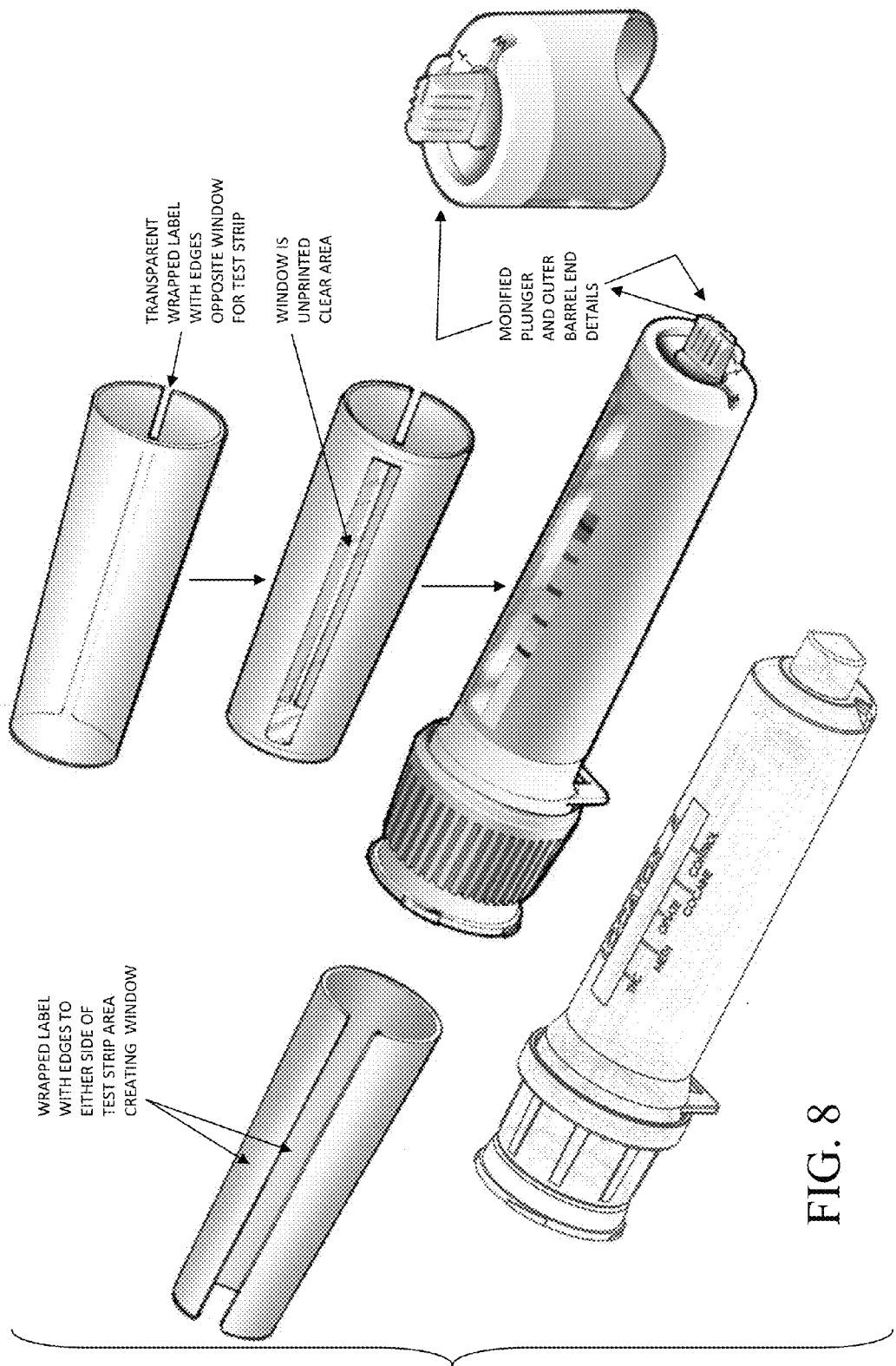
FIG. 8 shows one example of the internal housing assembly utilizing various sleeve inserts for labeling and viewing test results.
Figure 11A:
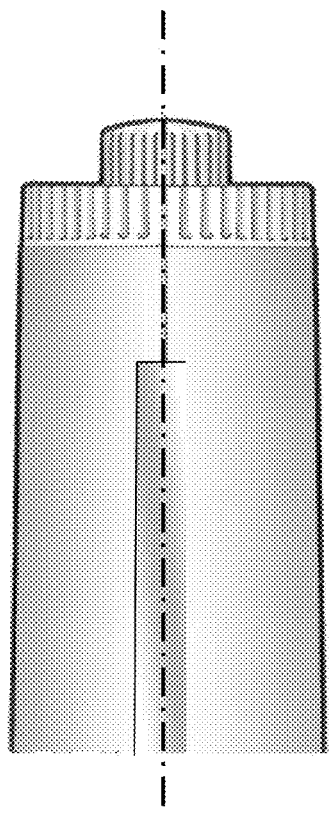
FIGS. 11A and 11B illustrate yet another embodiment of a button design, similar to that of FIGS. 7A-C, but utilizing a rounded button.
Figure 11B:
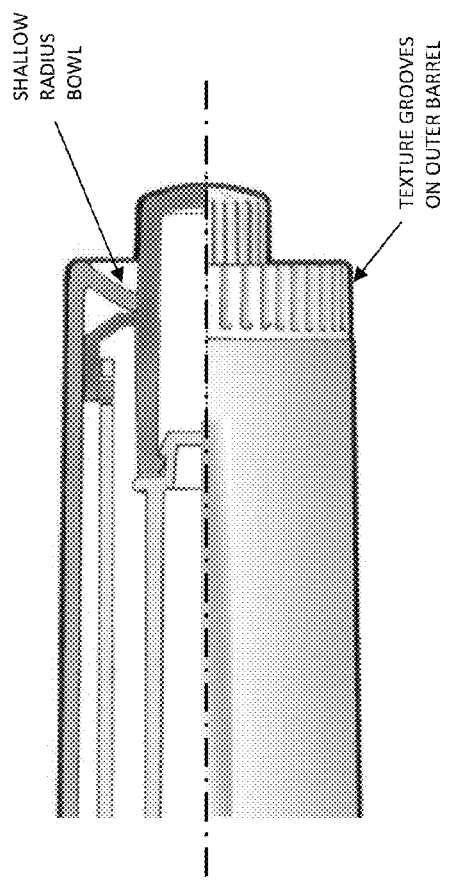
Figure 12C:
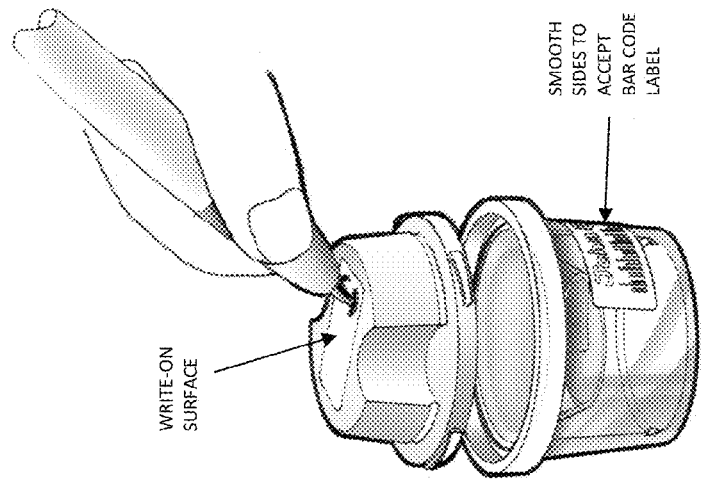
FIGS. 12A-12C illustrate alternative embodiments of a cap and nested lid arrangement.
Figure 12B:
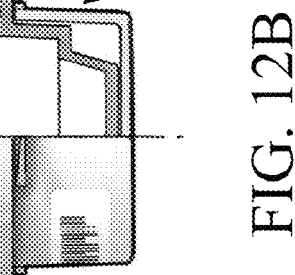
Figure 12A:
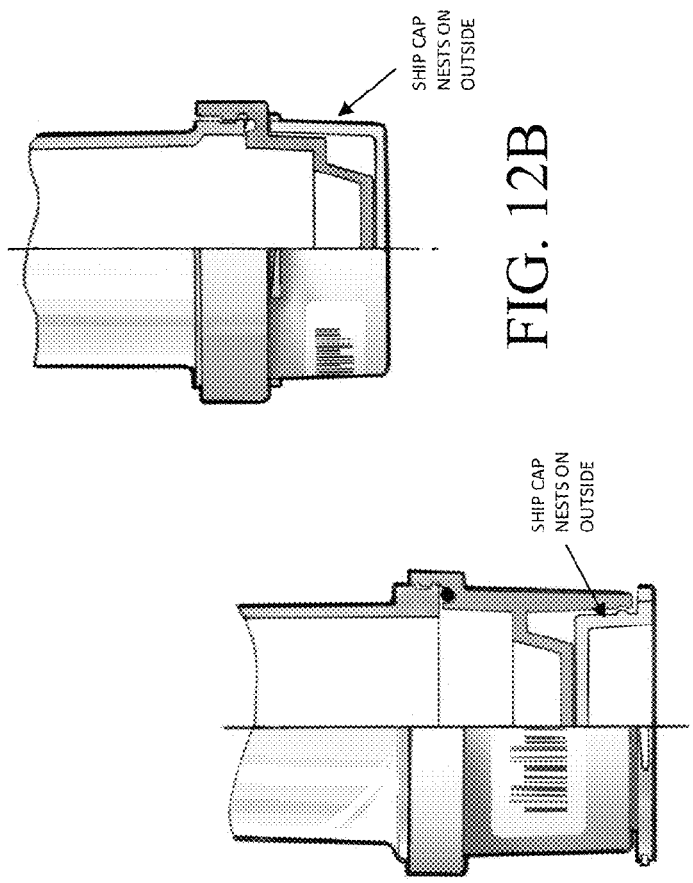
Figure 13:
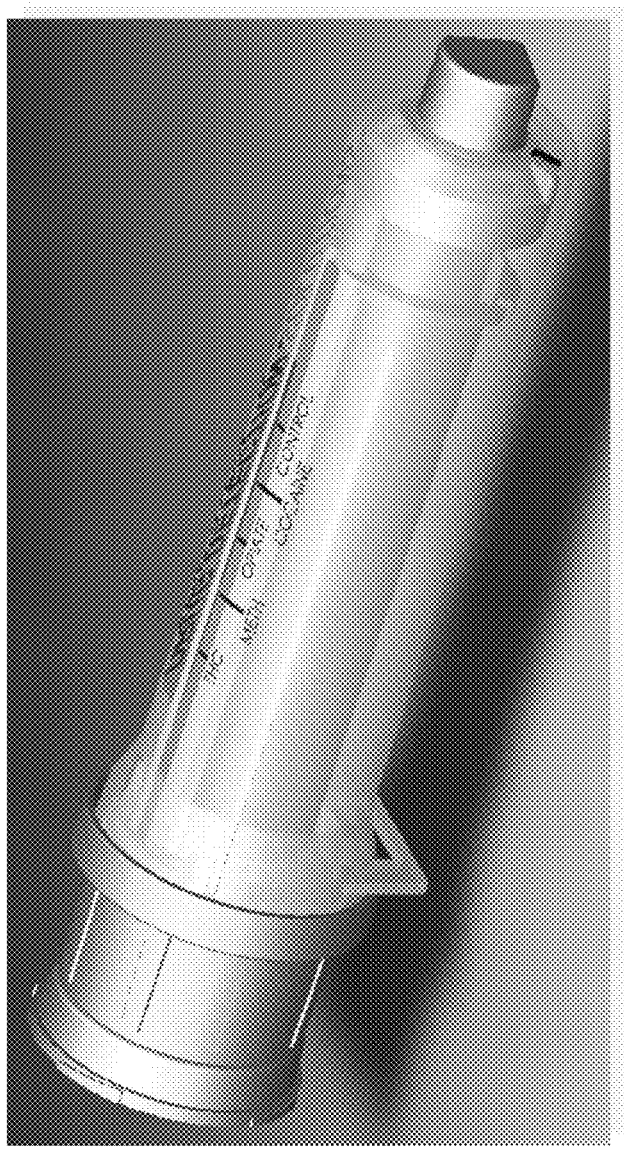
FIG. 13 is an illustration of a specific design embodiment of the subject invention.

To facilitate the collection of certain types of samples, it can be helpful if the swab 11 FIGS. 5A-B is wet or at least damp. In one embodiment, the main body contains a retention chamber or inner tube from which a wetting fluid can be released from a puncturable container onto the swab to assist in collecting a sample. Thus, the swab can be dry for obtaining certain types of samples (e.g., from a surface). But, if necessary or desirable, the wetting fluid can be released from the main body to wet the swab. Alternatively, as will be discussed in more detail below, a retention well 8 FIG. 5B within the cap 7 can be designed to contain a wetting fluid. In one embodiment, the wetting fluid can be released by puncturing a seal on the retention well. In a further embodiment, the swab is designed to puncture the seal.

In certain embodiments, the main body can be sealably coupled to the cap to prevent fluid leakage. In a specific embodiment, the main body includes a rectangular collar 6 that corresponds to rectangular openings in the cap 7. When the main body is joined to the cap, the collar engages with the openings, so as to form a seal that prevents liquid from leaking out of the housing unit. In a further embodiment, the rectangular collar 6 prevents the cap 7 from rotating about the main body.

In a related embodiment, the cap 7 FIGS. 4A-B includes an eluent fluid retention well 8 having a) at least one opening; b) at least one moveable sealing mechanism 10 over the opening that prevents the eluent fluid in the retention well from escaping and coming into contact with the collection/analysis material when the cap is placed over the main body of the housing unit; and c) a release mechanism 9 coupled/to the sealing mechanism(s) that, when acted upon by the operator, causes the sealing mechanism(s) to move from the opening and allow the eluent fluid in the retention well to flow through the opening(s) and come into contact with the collection/analysis material.

In certain embodiments, as illustrated in FIGS. 3A-C, the sealing mechanism 10 is a disc disposed over an opening 13 offset to one side of the eluent retention well 8. The disc has an opening 14 therethrough that corresponds to the opening in the eluent retention well 8 and a release mechanism that is a latch 9 attached to the disc. Utilizing the latch, the disc, being positioned sealably against the eluent retention well 8, can be rotated from between approximately 30° to approximately 180°, such that in a "closed" position, the disc 10 is positioned so that the opening 14 unaligned with the opening in the retention well 8. When desirable to release the eluent, such as, for example, after a sample has been taken, the latch 9 can be slideably rotated, such that the opening in the disc 14 aligns with the retention well opening 13 allowing the release of the eluent fluid.

In another embodiment, as illustrated in FIGS. 4A-B, the eluent is contained within a bag, pouch, balloon, or similar flexible or otherwise puncturable sealed receptacle 15 comprising a penetrable material or membrane. In one embodiment, the sealed receptacle 15 fills approximately ¼ to approximately ¾ the volume of the retention well 8 in the cap 7. In a more specific embodiment, the sealed receptacle 15 fills approximately ½ the volume of the retention well 8 with the cap 7.

In an alternative embodiment, the bag, pouch, balloon, or similar flexible or puncturable sealed receptacle comprising a penetrable material is contained within the housing. In a still further alternative embodiment, shown, for example, in FIGS. 6A-D, an inner tube 50 is contained within the housing that has disposed therein a fluid tube 55 having portion thereof comprising a penetrable material. In a specific embodiment, the end of fluid tube 55 nearest the swab comprises a penetrable material.

In a further embodiment, also shown, for example, in FIGS. 4A-B, the cap 7 includes a release mechanism 10 capable of puncturing the sealed receptacle 15. In one embodiment, the release mechanism 10 comprises a stylet, needle, prong, or similar elongated, sharpened implement for puncturing the sealed receptacle 15 and releasing the eluent into the retention well 8. FIGS. 4A-B, 7A-C, and 8 illustrate an embodiment wherein a plunger or button 9 on the exterior of the cap 7 can be depressed, turned, pressed, or otherwise activated by an operator, causing the sharp ended release mechanism 10 to be pushed into the sealed receptacle 15, puncturing the sealed receptacle and releasing the eluent into the retention well 8. In alternative embodiment, an example of which is shown in FIGS. 6A-D, the button 9 can be pressed or "fired" to advance the inner tube 50 towards an inner ring 42 having a sharpened prong 54 thereon for puncturing the penetrable material of the sealed receptacle, or on the inner tube 50 (as mentioned above), within the housing so that the eluent therein washes over the swab and into the cap 7. In a further embodiment, the button 9 is aligned to an appropriate position prior to being fired. And in a still further embodiment, an example of which is shown in FIGS. 7A-C and 9A-B, the button can be surrounded by a collar 58 that can aid in aligning the button to the appropriate position. As seen in the examples in FIGS. 1, 5A-B, 6A-D, 7A-C, and 11A-B, a variety of styles and configurations can be employed for the plunger or button 9 utilized with the subject invention. It would be well within the skill of a person trained in the art to create alternative button or plunger styles or configurations that can be utilized with the devices of the subject invention. Such variations are considered to be within the scope of the subject invention.

In certain other embodiments, the main housing includes additional aspects to assist the operator in using the single device system. For example, the housing can further include a timer 1 that is activated by a pressure switch located on the main body of the housing unit and/or reporting means for communicating the time to the operator. In a further embodiment, a conductive labeled probe, as described above, will close an open circuit triggered by the operator when the timer is started. Once the timer is triggered, if the test is positive the conductive labels will close the open circuit indicating a digital readout of positive or negative. Also, in certain applications quantitative results can be obtained if standards of known quantities are tested along with the unknown analyte.

In a method of use, an operator would utilize the single self-contained device system of the invention to detect the presence of an analyte on a solid surface by a) removing the cap from the main body of the housing unit; b) obtaining a sample analyte by bringing the collection/analysis material in contact with a solid surface to be tested; c) replacing the cap over the collection/analysis material and the main body of the housing unit; and d) releasing the eluent fluid from the retention well by triggering the release mechanism(s) on the cap.

In a more specific embodiment of a method of use, one embodiment of the device of the subject invention can be used to detect the presence of an illicit drug on a solid surface by:

a) removing the cap from the main body of the housing unit;

b) obtaining a sample analyte by bringing the swab attached to the device in contact with a solid surface to be tested and wiping an area of the surface. Instructions included with specific devices of the subject invention can provide information about the size of area to be wiped, such as a few inches, the approximate number of times to wipe an area, such as ten times, and other procedural details;

c) replacing the cap over the swab and securing it to the main body of the housing unit;

d) turning a button, as described above, to a first position;

e) depressing the button to puncture a tube or other receptacle containing an eluent within the housing, causing it to wash over the swab and into the cap;

f) agitating the sealed device vigorously for at least 5 seconds;

g) turning the button to a second position;

h) depressing the button again to introduce an analysis material within the housing to the analyte/eluent mixture for a pre-determined period of time, such as, for example, 5 seconds;

g) observing the results area on the housing after a pre-determined period of time, such as, for example, 3 minutes, to visually ascertain the results of the test.

In certain embodiments, one or several lateral flow strips (2-5 or more) are lined up in the housing unit on a platform 46 that is moveable by pressing down on a release button with the operators thumb. FIGS. 6A-D illustrate one embodiment utilizing a platform 46 for holding at least one lateral flow strip. The cap retention well has the eluent fluid retained by a foil seal. In operation the cap would be removed revealing the swab. The area to be tested would be swabbed and then the foil seal removed from the cap and the cap replaced on the device. It is shaken or agitated to release the material from the swab then the lateral flow strips are introduced to the elution fluid by the operator pushing the release button on the platform and sliding the platform with the strips into the cap with the elution fluid.

In other embodiments of the invention, the housing unit comprises a removable cap 7 that includes a retention well 8 in which eluent fluid is contained; a swab 11 on a moveable, solid support 30; an analysis material 3; and a results area 12. As illustrated in FIG. 5B, the retention well can include a self sealing membrane 40 that is positioned such that the swab 11 and moveable solid support 30 can penetrate through the membrane and access the eluent fluid. The housing unit preferably includes a means for limiting the movement of the solid support 50, such that following penetration through the self-sealing membrane, the swab cannot be moved beyond the retention well. The means for limiting movement 50 can include any of a variety of devices and techniques known to the skilled artisan for preventing further manual manipulation of a device following activation. For example, those systems used in hypodermic needles or other syringe devices that limit the plunger in order to prevent an operator from withdrawing and/or re-administering fluids after use of the needle or syringe can equally be applied to the device of the subject invention.

Self-sealing membranes are well known in the art. Examples of self-sealing membranes that can be used in accordance with the subject invention include those that are used with intravenous bags including, but not limited to, U.S. Pat. Nos. 5,400,995 and 6,805,842. In one embodiment of the invention, the self sealing membrane consists of an "O"-ring that enables the swab to penetrate there through and also has the ability to seal shut following removal of the swab. The size of the "O"-ring will depend upon the amount of target analyte the device is manufactured to test and thereby the size of the swab. The "O"-ring can be made of rubber, encapsulated, PTFE, Viton®, Kalrez Silicone or other standard materials used by those familiar with art.

In a method of use FIGS. 5A-B, the swab 11 is moved by the operator, so as to puncture the self sealing membrane 40 and enable the swab 11 to be immersed in the eluent fluid. The cap 7 is then removed and the wetted swab is swiped over a solid surface to be tested. Due to the nature of the self sealing membrane 40, following removal of the swab, the membrane 40 becomes sealed shut to ensure no release of the eluent fluid from the retention well 8. Following sampling of a solid surface, the cap 7 is replaced over the swab 11 and the swab 11 re-pierces the self sealing membrane 40 to allow any target analytes (such as illicit drugs) to be washed into the eluent. Through capillary action the analyte laden eluent is carried through the swab, and exposed to the analysis material 3 within the main body of the housing unit, and the results of that interaction are provided to the operator in the results area of the housing unit.

In yet another embodiment of the invention, as illustrated in FIG. 5A, the housing unit does not include a removable cap. In this embodiment, main body of the housing unit includes the retention well 8 in addition to the swab on a movable solid support, the analysis material, and the results area. The retention well houses the eluent fluid and includes two repuncturable self sealing membranes 40, 45. The two repuncturable self sealing membranes 40, 45 are located such that the swab can easily puncture there through.

With the above embodiment, as illustrated in FIG. 5A, the device is activated and used by puncturing a proximal self-sealing membrane 40 using the solid support 30 of the swab 11. The swab 11 is wetted by the eluent fluid within the retention well 8. The solid support 30 of the swab 11 is then advanced further so as to cause the swab 11 to penetrate a distal, repuncturable, self sealing membrane 45 to expose the swab to the outside of the housing unit. The wetted swab can then be swiped over a solid surface for testing or left exposed to collect target analytes in air. The solid support 30 is then moved to withdraw the swab 11 back into the retention well 8 and to allow the eluent fluid to wash any target analytes from the swab. As with the other embodiments described herein, through capillary action, the sample-eluent fluid is exposed to the analysis material within the main body of the housing unit and results are provided to the operator in the results area.

The eluent fluid can include, but is not limited to, distilled, sterile water or buffer solution that is conventionally used in immunoassays and familiar with those skilled in the art.

In preferred embodiments, as illustrated in FIG. 1, the collection and analysis materials are one and the same, where the single collection/analysis material includes in series, a number of zones (predefined areas): a collection (receiving) zone 11; a conjugate zone 5; a reaction zone (also referred to as a detection zone) 4; and optionally, a control zone. A medium is contacted with the collection/receiving zone (e.g., by wiping the collection zone on a solid surface), the collection/receiving zone is contacted with the eluent fluid via operator manipulation of the releasing mechanism on the cap, where the target analyte is washed from the collection/receiving zone into the eluent fluid to form a solvent.

As the solvent front migrates along the solid support, it carries the sample through the conjugate zone, which contains free probes specific for target analytes. Preferably, the probes are labeled with nanoparticles associated with differently colored dyes (e.g., red and blue dyed nanoparticles) and/or conductive particles. All of these components (potentially including bound labeled probes, and unbound probes) flow onto the capture zone, which contains immobilized binding agents (e.g., polyclonal antibodies) specific for the target analytes. Preferably, the binding agents immobilized in the capture zone are present in a 1:1 ratio. The nanoparticles will become fixed in the capture zone, and the shade of color can be read to indicate the presence of the target analyte or an open circuit closed by conductive particles.

In a further embodiment, one or more binding agents are immobilized in the reaction zone of the solid support. The binding agents may be immobilized by non-specific adsorption onto the support or by covalent bonding to the support, for example. Techniques for immobilizing binding agents on supports are known in the art and are described for example in U.S. Pat. Nos. 4,399,217, 4,381,291, 4,357,311, 4,343,312 and 4,260,678, which are incorporated herein by reference. Such techniques can be used to immobilize the binding agents in the invention. In one embodiment, the solid support is polytetrafluoroethylene, which makes it possible to couple hormone antibodies onto the support by activating the support using sodium and ammonia to aminate it and covalently bonding the antibody to the activated support by means of a carbodiimide reaction (yon Klitzing, Schultek, Strasburger, Fricke and Wood in "Radioimmunoassay and Related Procedures in Medicine 1982", International Atomic Energy Agency, Vienna (1982), pages 57-62.).

The analysis material upon which the probes and binding agents are provided include, but are not limited to, cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. The selection of an appropriate inert support is within the competence of those skilled in the art, as are its dimensions for the intended purpose.

Preferably, the analysis material is of a solid support that has an absorbent pad or membrane for lateral flow of a liquid medium to be assayed, such as those available from Millipore Corp. (Bedford, Mass.), including but not limited to Hi-Flow Plus™ membranes and membrane cards, and SureWick™ pad materials.

The amount of probe deposited on the analysis material will be selected so as to meet the requirement for use of a trace amount relative to the eluent fluid, as explained above. The binding agent must, as stated above, be one that is specific to the analyte as compared to all other materials it is likely to encounter in use, so that no interfering reaction or in-activation occurs, but this obstacle is no different in principle from those faced in in vitro assays of body fluids and successfully solved. The choice of a probe satisfying these criteria is thus within the general competence of those skilled in the art.

In certain embodiments, a control zone is provided that contains immobilized binding agents (e.g., immobilized polyclonal antibody) specific for the probe (e.g., goat anti-mouse IgG) used to label one of the target molecules, and will serve as a positive control to show that active material (e.g., monoclonal antibody) was carried the full distance to the analysis material.

The subject invention further includes a method for manufacturing a single device system for collecting, transferring, extracting, and testing for the presence of an illicit drug from a sample taken from a solid surface area and/or air or fluid samples. The method comprises providing a housing unit comprising a main body and cap that can be removably coupled to the main body; disposing a collection/analysis material in the housing; disposing a retention well within the cap; and disposing an eluent fluid within the retention well within the cap. FIGS. 9-13 illustrate various specific design embodiments of the devices of the subject invention that incorporate the various components and features described herein.

It will be further appreciated by the skilled artisan that more than one collection and analysis material can be included in the main body to form a multi-test system. Further, the single device systems and methods of the invention may be utilized in research and various industries, such as environmental management (e.g., water and wastewater treatment systems), bioremediation (e.g., to determine optimum conditions for microbial growth), public health (e.g., identification of rapidly growing infectious microbes), and homeland security (e.g., identification of rapidly growing bioterrorism agents, WMD and explosive agents.).

The device and method of the invention can be used in the area of chemical warfare, to assess the extent of exposure to sulfur mustard in the eyes, skin, and respiratory tract (e.g., lungs). The molecule(s) targeted for detection and/or measurement can be sulfur mustard reaction products such as alkylated serum proteins (e.g., albumin), alkylated hemoglobin, alkylated tear proteins (e.g., lactoferrin), alkylated epidermal proteins (keratins), alkylated lung fluid proteins, hydrolysis products of sulfur mustard in urine (thiodiglycol).

The device and method of the invention can be used to assess the presence of respiratory infection. The molecule(s) targeted for detection and/or measurement can be those associated with viruses, fungi, or bacteria (e.g., viral, fungal, or bacterial antigens) that cause pulmonary infections, such as respiratory syncytial virus influenza virus, and pseudomonas.

In certain embodiments, a system is provided that incorporates the use of the device of the invention. The detection system includes a reporting means capable of tracking the presence and/or concentration of detected target analyte(s) as determined from the single self-contained device analysis. In related embodiments, the single self-contained device described herein includes a computerized means for reporting and tracking target analyte qualitatively or quantitative levels of concentrations. Preferably, the computerized means is capable of communicating remotely or proximately as well as being capable of providing the necessary outputs, controls, and alerts to the operator.

In a preferred embodiment, the single self-contained detection devices are provided as small, handheld portable equipment. It can be used by an operator in the home, at work, in airports or other security checkpoints. In certain embodiments, such devices can be designed for continuous monitoring, such as at the office, in the operating room, etc. where this capability would be valuable.

According to the subject invention, an illicit drug testing kit is provided for testing a solid surface area for illicit drug residues. A kit of the invention contains the necessary material for performing the methods described herein. This kit may contain any one or combination of the following, but is not limited to, a single self-contained testing device, which includes a housing unit having a main body, a swab, an analysis material based on, but not limited to, lateral flow analysis technology, and a results area; a set of subject instructions for its use; and optionally a means for forensic sealing the device for transport to a laboratory for further confirmatory testing also envisioned is a wireless computer device for keeping track of, storing, displaying, and/or communicating monitored results. In certain related embodiments, the device can calculate and display the concentration of detected illicit drugs present in the matrix tested e.g. surfaces, pills, capsules, unknown powders, air or fluids.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A device for collecting, extracting, testing and identifying an analyte from a sample, the device comprising:
   a main body comprising a hollow interior;
   at least one swab positioned at a first end of the main body for obtaining a sample;
   at least one sealed receptacle disposed within the main body and having therein an eluent for dissolving an analyte;
   a release mechanism capable of being engaged with the sealed receptacle to release the eluent;
   a cap removably attached to the first end of the main body and having a hollow depression therein for receiving released eluent, such that an analyte on the swab is dissolved into the eluent;
   at least one analysis strip disposed within the main body having thereon at least one conjugate zone and at least one reaction zone, whereby the presence or absence of an analyte within the eluent triggers at least one reaction zone to exhibit a noticeable signal, and
   a button operably engaged with the main body, such that, when aligned in a first position and activated by depressing, the button engages the sealed receptacle with the release mechanism, such that the swab is exposed to the eluent, so as to dissolve analyte thereon and when the button is aligned in a second position, and depressed, causes the at least one analysis strip to be exposed to the dissolved analyte.

2. The device, according to claim 1, wherein the sample is obtained from a surface, liquid, or air.

3. The device, according to claim 1, wherein more than one analyte can be tested for in the eluent.

4. The device, according to claim 1, further comprising a lid for sealing the cap.

5. The device, according to claim 1, wherein the noticeable signal s visible or audible.

6. The device, according to claim 5, further comprising a results area on the main body for observing a visible signal.

7. The device, according to claim 1, wherein the release mechanism is an inner ring having a prong fixedly attached thereon for puncturing the sealed receptacle.

8. The device, according to claim 7, wherein the sealed receptacle is a fluid tube disposed within an inner tube to which the button is operably engaged.

9. The device, according to claim 1, wherein the analysis strip is a lateral flow analysis strip.

10. The device, according to claim 9, further comprising a control zone on the analysis strip.

11. The device, according to claim 1, wherein the swab comprises polyester treated with sodium tetraborate in a nonionic surfactant having pH 8.6.

12. The device, according to claim 1, wherein the eluent fluid comprises distilled sterile water or a buffer solution.

13. The device, according to claim 1, wherein the analyte is selected from the group consisting of: amphetamines, barbiturates, benzodiazepines, cannabinoids, cocaine, opiates, phencyclidine and their metabolites.

14. The device, according to claim 1, wherein the analyte is the parent compound of THC ($\Delta^9$-tetrahydrocannabinol), cocaine or heroin.

15. The device, according to claim 1, further comprising a platform for supporting the analysis strip and operably engaging the analysis strip with the button.

* * * * *